United States Patent
Seo et al.

(10) Patent No.: US 6,916,788 B2
(45) Date of Patent: Jul. 12, 2005

(54) LIQUID COMPOSITION OF BIODEGRADABLE BLOCK COPOLYMER FOR DRUG DELIVERY SYSTEM AND PROCESS FOR THE PREPARATION THEREOF

(75) Inventors: Min-Hyo Seo, Seo-ku (KR); In-Ja Choi, Daejeon (KR)

(73) Assignee: Samyang Corporation, Seoul (KR)

( * ) Notice: Subject to any disclaimer, the term of this patent is extended or adjusted under 35 U.S.C. 154(b) by 74 days.

(21) Appl. No.: 10/169,012

(22) PCT Filed: Dec. 21, 2000

(86) PCT No.: PCT/KR00/01508

§ 371 (c)(1),
(2), (4) Date: Jun. 22, 2002

(87) PCT Pub. No.: WO01/45742

PCT Pub. Date: Jun. 28, 2001

(65) Prior Publication Data

US 2003/0082234 A1 May 1, 2003

(30) Foreign Application Priority Data

Dec. 22, 1999  (KR) ........................................ 1999-60349

(51) Int. Cl.[7] ........................... A61K 38/00; A61K 9/14
(52) U.S. Cl. ......................................... 514/12; 424/486
(58) Field of Search .................. 424/486, 435, 424/427, 450, 78.22, 449, 426, 425, 424; 514/12, 2; 530/350; 528/272, 275

(56) References Cited

U.S. PATENT DOCUMENTS

| | | | | |
|---|---|---|---|---|
| 4,844,896 A | * | 7/1989 | Bohm et al. | 424/93.461 |
| 5,384,333 A | | 1/1995 | Davis et al. | 514/772.3 |
| 5,599,552 A | | 2/1997 | Dunn et al. | 424/423 |
| 5,607,686 A | | 3/1997 | Totakura et al. | 424/426 |
| 5,612,052 A | | 3/1997 | Shalaby | 424/426 |
| 5,702,717 A | * | 12/1997 | Cha et al. | 424/425 |
| 5,958,445 A | * | 9/1999 | Humber et al. | 424/439 |
| 6,616,941 B1 | * | 9/2003 | Seo et al. | 424/450 |

OTHER PUBLICATIONS

Kim et al. Methoxy poly(ethelene glycol and e–caprolactone amphillic block copolymeric micelle containing indomethacin., 1998, Journal of controlled release, 51, 13–22.*

* cited by examiner

Primary Examiner—Jon Weber
Assistant Examiner—Robert B. Mondesi
(74) Attorney, Agent, or Firm—Edwards & Angell, LLP (57) ABSTRACT

The present invention relates to a liquid polymeric composition capable of forming a physiologically active substance-containing implant when it is injected into a living body and a method of preparation thereof. The composition comprises a water-soluble biocompatible liquid polyethylene glycol derivative, a biodegradable block copolymer which is insoluble in water but soluble in the water-soluble biocompatible liquid polyethylene glycol derivative and a physiologically active substance.

33 Claims, 2 Drawing Sheets

LIQUID COMPOSITION OF BIODEGRADABLE BLOCK COPOLYMER FOR DRUG DELIVERY SYSTEM AND PROCESS FOR THE PREPARATION THEREOF

FIELD OF THE INVENTION

The present invention relates to a liquid composition for drug delivery. More specifically, the present invention relates to a liquid polymeric composition comprising a water-soluble, biocompatible, liquid polyethylene glycol derivative; a biodegradable block copolymer which can be dissolved in the liquid polyethylene glycol derivative but which can not be dissolved in water; and a physiologically active substance, wherein when injected into a living body, the composition forms a polymeric implant containing the physiologically active substance that gradually releases the physiologically active substance and then decomposes into materials harmless to the human body.

BACKGROUND OF THE INVENTION

Biocompatible, biodegradable polymers have been widely used in the medical field as surgical sutures, tissue regenerative induction membranes, protective membranes for the treatment of wounds, and drug delivery systems Among biodegradable polymers, polylactide (PLA), polyglycolide (PGA) and a copolymer (PLGA) of lactide and glycolide have been the subject of many studies and are commercially available since they have good biocompatibility and are decomposable in the body to harmless materials such as carbon dioxide, water, etc.

One example of a biodegradable polymeric drug delivery system is a system wherein a drug is contained in a biodegradable polymer matrix which has the disadvantage of having to be implanted via surgery. In the form of injectable drug delivery systems, polymeric microspheres and nanospheres are known in the art. However, those systems have disadvantages in that they require special preparation methods. In addition, since the biodegradable polymers used can only be dissolved in organic solvents preparation requires the use of organic solvents harmful to the human body and therefore any residual solvent remaining after preparation of the microspheres must be completely removed. Furthermore, some drugs such as polypeptides and proteins may lose their physiological activity after contacting organic solvents.

U.S. Pat. No. 5,384,333 discloses an injectable drug delivery composition in which a pharmacologically active substance is contained in a copolymer comprising a hydrophilic part and a hydrophobic part. The composition is in a solid state at temperatures ranging from 20° C. to 37° C. and is in a fluid state at temperatures ranging from 38° C. to 52° C. The composition has to be heated to a relatively high temperature such as 38° C. to 52° C., immediately before use and it is difficult to uniformly distribute the drug in the polymeric composition.

U.S. Pat. No. 5,612,052 discloses a block copolymer composition characterized by a hydrophobic polyester (A) and a hydrophilic polyethylene oxide (B) which are combined in the form of an A-B-A triblock, which is then hydrated by contacting it with water which then forms a hydrogel However, the drug incorporated in this composition is rapidly released and therefore a special means of using separate biodegradable fine particles containing the drug, in the form of a suspension, is required.

U.S. Pat. No. 5,702,717 discloses a system for delivery of proteins containing A-B-A type block copolymers comprising hydrophobic biodegradable polyesters (A) and hydrophilic polymeric polyethylene oxide (B), which undergo sol-gel phase transition in an aqueous solution at particular temperatures and concentrations. This system takes advantage of a thermal property of the block copolymers in that they are dissolved in water at temperatures below 20° C. and undergo phase transition to form a gel at temperatures above about 30° C. Thus, this system uses a composition in which the drug is dissolved together with the polymers in an aqueous solution at low temperatures, the resulting solution is then injected into a human body via a syringe. At body temperature the polymers undergo phase transition to form a gel and then the drugs incorporated therein is slowly released. Since the polymers are biodegradable, the preparation of this composition does not require the use of organic solvents or any special methods and the composition can be simply sterilized by using a membrane filter. However, this method has several drawbacks in that since the constituents of the block copolymers are degradable polymers and can be hydrolyzed with water, they cannot be commercialized in the form of a polymeric aqueous solution. In addition, since the composition needs to be dissolved in water before use which requires more than half an hour, it is difficult for this composition to be converted into a commercial product. Furthermore, since water is the main constituent, although it is suitable as a delivery system for the long term administration of peptide or protein medicines and drugs which are sparingly soluble in water, it is not a suitable composition to be used as a biodegradable implant since aqueous monomolecular medicines are rapidly released over short periods of time.

U.S. Pat. No. 5,599,552 discloses a composition wherein a water-insoluble biodegradable thermoplastic polymer is dissolved in a water-miscible organic solvent, and the resulting composition can be implanted where it then undergoes a phase transition when in contact with water or body fluids. However, the drawback is that it is difficult to use because a mono-molecular organic solvent is used to dissolve the biodegradable thermoplastic polymer. Most mono-organic solvents, such as N-methyl-2-pyrrolidone, ethyl lactate, dimethylsulfoxide, etc., cause side effects such as cell dehydration and tissue necrosis, etc. and they may also cause severe pain at the application sites.

U.S. Pat. No. 5,607,686 discloses a liquid polymeric composition prepared by mixing a hydrophilic liquid polymer, instead of a mono-molecular organic solvent, with a water-insoluble hydrophobic polymer. When contacted with water the composition undergoes a phase transition and forms an implant and thus it does not cause a the rapid volume reduction and it has no special side effects due to the good cyto-compatibility of the low molecular weight polyethylene oxide. However, the water-insoluble hydrophobic polymers used are not biodegradable. In addition, the preparation of the composition requires heating to about 80° C. in order to achieve uniform mixing of the water-insoluble hydrophobic polymer and the hydrophilic liquid polymer. Therefore, this system may be suitable to use for adherence prevention and wound protection without any physiologically active substance, but it is not suitable for delivery of physiologically active substances, particularly peptide or protein medicines because peptide and protein medicines lose their activities at high temperatures. Furthermore, protein medicines are water soluble, thus it is very difficult to uniformly incorporate them into the composition. In addition, it is not disclosed in this patent how the drugs or physiologically active substances can be uniformly incorporated in the polymeric composition. Particularly, although polylactide, polyglycolide and their copolymers can be mixed with polyethylene glycol at high temperatures of 80° C. in order to obtain a uniform composition, the composition undergoes phase separation when it stands for a long period of time due to the lowered affinity of the polylactide, the polyglycolide or their copolymers with polyethylene glycol. Therefore, it is very difficult to maintain a uniform composition.

Sterilization steps are necessary in the preparation of implant formulations. Existing sterilization methods are unsuitable for implant formulations due to properties of the implant compositions or because the methods are uneconomical or too complicated. For example, it is almost impossible to prepare a uniform solution by mixing a drug, a water-insoluble biodegradable polymer and a hydrophilic polymer. Therefore, the composition cannot be sterilized by simple methods such as membrane filtration, and must be sterilized by radiation exposure or EO (ethylene oxide) gas methods. However, radiation may cause damage to the drug and the EO gas method is pharmaceutically unacceptable as a method to sterilize the implant formulation. Furthermore, although the formulation may be prepared under sterilized conditions, such methods are very expensive to the extent that the practicability of the preparation may be lowered. Thus, a composition for use as an implant which can be prepared by a simple procedure, and which releases the drug over a long period and which is administered by a single injection and which can decompose into materials harmless to human body is needed.

DISCLOSURE OF THE INVENTION

The present invention provides a liquid composition of a drug delivery implant, which slowly releases the active substance over a prolonged period, which is administered by a single injection and which can then decompose into materials harmless to the human body and be excreted. The liquid polymeric composition of the present invention comprises a water-soluble biocompatible liquid polyethylene glycol derivative, a biodegradable block copolymer, which is insoluble in water but soluble in the water-soluble biocompatible liquid polyethylene glycol derivative, and a pharmacologically or physiologically active substance The present invention is directed to a liquid polymeric composition containing a water-soluble biocompatible liquid polyethylene glycol derivative, a biodegradable block copolymer which is water-insoluble but which can be dissolved in the water-soluble biocompatible liquid polyethylene glycol derivative, and a pharmacologically and physiologically active substance. The liquid composition of the present invention forms a polymeric implant, containing a physiologically active substance, which, when it is injected into a living body, then slowly releases the active substance over a prolonged period of time and is then decomposed into materials harmless to the human body and excreted.

The biodegradable block copolymer is a polymer which is not dissolvable in an aqueous solution but is dissolvable in a low molecular weight polyethylene glycol or derivative thereof The biodegradable block copolymer can be hydrolyzed with water to materials harmless to human body, and serves as a drug reservoir when administered. This copolymer is preferably a block copolymer formed by ester bonding of a hydrophobic polyester (A) block and a polyethylene glycol (B) block. The biodegradable block copolymer is a di- or tri-block copolymer comprising biodegradable hydrophobic polymer A block component and a hydrophilic polymer B block component The type of block linkage of the copolymer can be A-B-A, B-A-B, A-B or (A-B)$_n$ where n is an integer of from about 2 to 20. The A-B-A type block is preferred. The molecular weight of the biodegradable block copolymer is preferably within the range of 1,000 to 50,000 Daltons, more preferably within the range of 1,000 to 15,000 Daltons and most preferably within the range of 1,000 to 10,000 Daltons.

The hydrophobic polyester (A) block can be a member selected from the group consisting of L-polylactide (L-PLA), D,L-polylactide (D,L-PLA), a copolymer of L- or D,L-lactide with glycolide (PLLGA or PDLLGA), polyglycolide (PGA), polycaprolactone (PCL), a copolymer of lactic acid with caprolactone (PLCL), polyhydroxy butyric acid (PHB), a copolymer of 1,4-dioxan-2-one with lactide (PLDO), and poly(p-dioxanone) (PDO). Preferably, the hydrophobic polyester (A) block is a member selected from the group consisting of L-polylactic acid (L-PLA), D,L-polylactic acid (D,L-PLA), a copolymer of L- or D,L-lactic acid with glycolic acid, and a copolymer of 1,4-dioxan-2-one with lactide. The molecular weight of the hydrophobic polyester (A) block is preferably within the range of 500 to 25,000 Daltons, more preferably within the range of 500 to 15,000 Daltons and most preferably within the range of 1,000 to 5,000 Daltons.

The hydrophilic polymer B block of the biodegradable copolymer is preferably a member selected from the group consisting of polyethylene glycol (PEG), a copolymer of ethylene glycol and propylene glycol and derivatives thereof More preferably, the hydrophilic polymer B block is a polyethylene glycol derivative. The molecular weight of the hydrophilic polymer B block is preferably within the range of 100 to 10,000 Daltons, and more preferably within the range of 500 to 5,000 Daltons.

In the biodegradable block copolymer, the content of the hydrophilic polymer B block is preferably within the range of 20 to 80 wt %, and more preferably within the range of 40 to 70 wt % In the liquid polymeric composition of the present invention, the content of the biodegradable block copolymer is preferably within the range of 5 to 80 wt %, and more preferably within the range of 20 to 60 wt % and most preferably within the range of 20 to 50 wt %.

The liquid polyethylene glycol derivative used in the present invention serves as a main constituent which dissolves or uniformly mixes with the biodegradable block copolymer and so reduces the viscosity of the total polymeric composition and increases the fluidity of the composition. Thus the polymeric composition can be readily injected by means of a syringe of 18 to 23 gauge. The liquid polyethylene glycol derivative can dissolve when in contact with water or body fluids allowing the biodegradable block copolymer, containing the physiologically active substance, to solidify as an implant. Therefore, the liquid polyethylene glycol derivative of the present invention should be a material which cause neither decomposition or changes the properties of the biodegradable block copolymer, and further, does not cause loss of activity of the physiologically active substance. The liquid polyethylene glycol derivative is in the form of a polymer which is a liquid at room temperature. Polyethylene glycol derivatives suitable for the present invention include polyethylene glycol, dialkyl polyethylene glycol, diacyl polyethylene glycol, etc., which has the following formula (I):

$$R^1\text{---}XCH_2CH_2(OCH_2CH_2)_l\text{---}X\text{---}R^1 \qquad (I)$$

in which $R^1$ is H, $(CH_2)_m CH_3$ or $CO(CH_2)_m CH_3$, wherein m is an integer of 0 to 17;

X is O, NH or S; and i is an integer of 1 to 100.

Preferably, the hydroxy groups of both ends of the liquid polyethylene glycol are protected to prevent them from decomposing the ester bonds of the polylactic acid or polyglycolic acid of the hydrophobic A block of the biodegradable block copolymer The hydroxy groups of polyethylene glycol can be protected by etherification with an alkyl group or esterification with an acyl group. Preferably, the hydroxy groups are protected by esterification so that they can be hydrolyzed with water to materials harmless to the human body. Esterification also increases the affinity of the liquid polyethylene glycol derivative for the biodegradable block copolymer and minimizes the phase separation in the liquid polymeric composition. Therefore, it is particularly preferred to use a polyethylene glycol derivative wherein ester groups are introduced in order to increase compatibility with the biodegradable block copolymer.

Preferably, the liquid polyethylene glycol derivative has an affinity for the biodegradable block copolymer and does not cause phase separation or induce the decomposition of the ester groups of the hydrophobic A block polymer. Examples of liquid polyethylene glycol derivatives include those having hydroxy groups at both ends which are protected with ester groups, and which are further esterified with dicarboxylic acid to increase the content of ester groups, as in the following formula (II):

$$R^2OOC(CH_2)_qC(O)(OCH_2CH_2)_p\text{—}OC(O)(CH_2)_qCOOR^2 \quad (II)$$

in which $R^2$ is $(CH_2)_xCH_3$, wherein x is an integer of 0 to 17, H, Na, Ca, Mg or Zn, p is an integer of 1 to 100; and q is an integer of 0 to 6.

The polymers of formula (II) above can be obtained by reacting polyethylene glycol with an anhydride of dicarboxylic acid such as malonic acid, succinic acid, glutaric acid, etc. to obtain dicarboxy polyethylene glycol which is treated with thionyl chloride to change the carboxy groups into acyl chlorides and then treated with an alcohol to obtain an ester Preferably, the molecular weight of the polyethylene glycol derivative is within the range of 100 to 15,000 Daltons, more preferably within the range of 200 to 1,000 Daltons. In the liquid polymeric composition of the present invention, the content of the liquid polyethylene glycol derivative is preferably within the range of 10 to 95 wt %, and more preferably within the range of 30 to 70 wt %.

In the composition of the present invention, the "physiologically active substance" or "the drug" refers to a substance which has a water solubility of 1 µg/ml or more and inhibits the growth of microorganisms, viruses, etc., or stimulates or inhibits the physiological function of a warm blooded animal or human body. Examples of such physiologically active substances (drug) include antibacterial agents, anti-inflammatory agents, anticancer agents, growth hormones, antimalarial agents, hormones, immunostimulants, growth factors, antipyretics, antidepressants, immunodepressants, antiemetics, agents for treatment of diabetes, antihypertensive agents, antihyperlipidemic agents, agents for treatment of cardiovascular disorders, and the like.

Typical examples of antibacterial agents which can be used in the present invention include minocycline, tetracycline, ofloxacin, phosphomycin, mergain, profloxacin, ampicillin, penicillin, doxycycline, thienamycin, cephalosporin, norcadicin, gentamycin, neomycin, kanamycin, paromomycin, micronomycin, amikacin, tobramycin, dibekacin, cefotaxim, cephaclor, erythromycin, ciprofloxacin, levofloxacin, enoxacin, vancomycin, imipenem, fucidic acid and mixtures thereof Examples of anticancer agents which can be used in the present invention include paclitaxel, taxotare, adriamycin, endostatin, angiostatin, mitomycin, bleomycin, cisplatin, carboplatin, doxorubicin, daunorubicin, idarubicin, 5-fluorouracil, methotrexate, actinomycin-D and mixtures thereof Examples of anti-inflammatory agents which can be used in the present invention include lysozyme, acetaminophen, aspirin, ibuprofen, diclofenac, indomethacin, piroxicam, fenoprofen, flubiprofen, ketoprofen, naproxen, suprofen, loxoprofen, cinoxicam, tenoxicam and mixtures thereof.

The present invention is particularly useful for delivering drugs, for example, peptide and protein drugs, which require daily administration for a long period of time, have a high molecular weight and are difficult to absorb through the gastrointestinal tract or skin. Examples of such drugs include human growth hormone (hGH), porcine growth hormone (pGH), leukocyte growth factor (G-CSF), erythrocyte growth factor (EPO), macrophage growth factor (M-CSF), tumor necrosis factor (TNF), epithelial growth factor (EGF), platelet-derived growth factor (PDGF), interferon-α, β, γ(IFN-α, β, γ), interleukin-2 (IL-2), calcitonin, nerve growth factor (NGF), growth hormone releasing factors, angiotensin, luteinizing hormone releasing hormone (LHRH), LHRH agonist, insulin, thyrotropin releasing hormone (TRH), angiostatin, endostatin, somatostatin, glucagon, endorphin, bacitracin, mergain, colistin, monoclonal antibody or vaccines, bone growth factor (BMP), etc.

The content of said physiologically active substance in the liquid polymeric composition of the present invention is preferably within the range of 1 to 40 wt %, and more preferably within the range of 1 to 30 wt % and most preferably within the range of 2 to 25 wt %.

The liquid polymeric composition of the present invention can further contain a pharmaceutically acceptable additive in order to improve the stability of the drug in the polymeric composition, and to control the concentration of hydrogen ion in the composition or to control the release rate of the drug and the decomposition rate of polymer Such additive is preferably selected from the group consisting of surfactants, inorganic salts, sugars, natural polymers and mixtures thereof. Either ionic or non-ionic surfactants may be used in the composition of the present invention, however, non-ionic surfactants are preferred. Typical ionic surfactants include sodium dodecylsulfate and typical non-ionic surfactants include polysorbate, polyvinylpyrrolidone, poloxamers, glyceryl monooleate, glyceryl monostearate, polyoxyethylene alkyl ether and mixtures thereof The sugars which can be used as additives in the present invention include mannitol, sorbitol, glucose, xylitol, trehalose, sorbose, sucrose, galactose, dextran, dextrose, fructose, lactose and mixtures thereof. Examples of inorganic salts which can be used as additives in the present composition include sodium chloride, calcium chloride, zinc chloride, magnesium chloride, calcium carbonate, zinc carbonate, zinc acetate, zinc lactate, magnesium hydroxide, aluminum chloride, aluminum hydroxide, zinc oxide and mixtures thereof. Examples of natural polymer which can be used as additives in the present composition include cyclodextrin, gelatin, albumin, hyaluronic acid, chitosan, sodium carboxymethylcellulose and mixtures thereof The content of additives in the liquid polymeric composition of the present invention is preferably within the range of 0.01 to 10 wt %, and more preferably within the range of 2 to 8 wt %.

The present invention also provides a formulation for an inplant comprising the liquid polymeric composition as mentioned above. The present invention includes an implant formed from the above liquid polymeric composition.

The liquid polymeric composition according to the present invention can be prepared by a process which comprises the steps of mixing and dissolving a water-soluble biocompatible liquid polyethylene glycol derivative, a biodegradable block copolymer which is insoluble in water but soluble in said water-soluble biocompatible liquid polyethylene glycol derivative, and a physiologically active substance, in an organic solvent or mixture of an organic solvent and water to obtain a polymeric solution wherein the ratio of the organic solvent and water is within the range of 0.2/0.8 to 0.8/0.2; sterilizing the polymeric solution by filtration through a membrane and removing the organic solvent by lyophilizing or evaporating the filtered polymeric solution under reduced pressure.

Alternatively, the liquid polymeric composition of the present invention can be prepared by a process which comprises the steps of preparing a solution of one or more member selected from the group consisting of a water-soluble biocompatible liquid polyethylene glycol derivative, a biodegradable block copolymer which is insoluble in water but soluble in said water-soluble biocompatible liquid polyethylene glycol derivative, and a physiologically active substance, in an organic solvent or mixture of an organic solvent and water to obtain a solution wherein the ratio of the organic solvent and water is within the range of 0.2/0.8 to 0.8/0.2; sterilizing the respective solution by filtration through a membrane, mixing the filtered solution and removing the organic solvent by lyophilizing or evaporating the mixed solution under reduced pressure.

Specifically, the liquid polymeric composition of the present invention can be prepared according to the following manner Firstly, the biodegradable block copolymer, the liquid polyethylene glycol derivative, the physiologically active substance and optionally the additives are dissolved together in an organic solvent or mixture of an organic solvent and water to prepare the polymer solution Examples of suitable organic solvents for preparing the polymer solution include acetonitrile, acetone, acetic acid, dimethyl acetamide, ethanol, isopropanol, dioxane, etc. Preferably, the organic solvent is used in combination with water with a mixing ratio of solvent to water within the range of about 0.2/0.8 to 0.8/0.2

Secondly, the resulting polymer solution is sterilized by filtering through a membrane filter having a pore size of 0.8 to 0.22 µm The organic solvent and water are then removed by lyophilization or evaporation, under reduced pressure, in preparation of the liquid polymeric composition. When the polymer solution containing the physiologically active substance is prepared by making the polymer solution out of an organic solvent and water, the resulting solution may be frozen and then lyophilized. The lyophilization is carried out by removing excess solvent from the solution at a temperature below 30° C., under a reduced pressure of below about 0.1 torr. The liquid polymeric composition is then dried by vacuum under reduced pressure until the water content is below 1%, and preferably below 0.5%. During vacuum drying, it is preferred that the liquid composition is stirred with a mixer so that the physiologically active substance can be uniformly distributed. If the organic solvent is used without water, the liquid composition is preferably slowly evaporated under reduced pressure without lyophilization.

The composition of the present invention may also be prepared by dissolving in the organic solvent, one or more components selected from the group consisting of the biodegradable block copolymer, the liquid polyethylene glycol derivative, the physiologically active substance and additives, to prepare the respective solution, which is then individually filtered through a membrane filter and then mixed to obtain the liquid composition of the present invention.

The liquid polymeric composition containing the physiologically active substance, according to the present invention, can be dispensed into a disposable syringe in the amount required for a single dose. The syringe is then sealed in order to prepare the ready-to-use drug-containing liquid polymeric composition for implanting Since, according to the present invention, the organic solvent is removed by evaporation, the liquid polymeric composition of the present invention eliminates the possibility of histotoxicity such as tissue dehydration, necrosis and pain that is caused by organic solvent when the composition is injected into tissues. In addition, since no water is contained in the liquid composition of the present invention, the hydrolysis of the biodegradable polymer can be prevented. Furthermore, since the biodegradable block copolymer is dissolved in low molecular polyethylene glycol, the composition can be sterilized by membrane filtration. The composition of the present invention forms an implant when injected. From the implant the drug can be slowly released. The implant is then decomposed into materials harmless to the human body and is then excreted after the drug release is completed.

BEST MODE FOR CARRYING OUT THE INVENTION

The present invention will be more specifically illustrated by the following preparations and examples. While the following preparations and examples are provided for the purpose of illustrating the present invention, they are not to be construed as limiting the scope of the present invention.

EXAMPLES

Preparation 1: Synthesis of Biodegradable Block Copolymers (1) Block copolymers (PLA-PEG-PLA) of polylactide (PLA) and polyethylene glycol (PEG), or block copolymers (PLGA-PEG-PLGA) of copolymer (PLGA) of lactide and glycolide and polyethylene glycol (PEG).

Lactide (14.19 g), glycolide (3.81 g), polyethylene glycol (molecular weight (MW) 1000, 7.5 g) and tin octoate (0.18 g), as the catalyst, were added to a two-necked, round-bottomed flask, which was then exposed to reduced pressure and filled with nitrogen gas. While heating at 120° C. to 145° C. with stirring, the mixture was reacted for 12 hours and then dissolved with chloroform. In order to precipitate the polymer, the resulting solution was then added to dry ether. The resulting polymer was separated, dissolved in chloroform and then purified by precipitating with ether. The precipitated polymer was separated and then dried under vacuum to obtain the block copolymers as shown in the following Table 1.

Other block copolymers shown in the following Table 1 can also be prepared according to the same procedure described above.

TABLE 1

| Block copolymer | LA/GA ratio | PEG MW (Daltons) | PEG (%) | MW (Daltons) A-B-A | Yield (%) |
|---|---|---|---|---|---|
| PLA-PEG-1 | 100/0 | 1000 | 31 | 1090-1000-1090 | 95 |
| PLGA-PEG-2 | 74/26 | 1000 | 28.8 | 1234-1000-1234 | 95 |
| PLGA-PEG-3 | 73/27 | 1000 | 46.3 | 580-1000-580 | 93 |
| PLGA-PEG-4 | 71/29 | 1000 | 50 | 500-1000-500 | 94 |
| PLGA-PEG-5 | 82/18 | 1000 | 36 | 890-1000-890 | 98 |
| PLA-PEG-6 | 100/0 | 3400 | 40 | 2500-3400-2500 | 96 |
| PLGA-PEG-7 | 70/30 | 8000 | 42 | 5500-8000-5500 | 94 |

Note)
LA = lactide, GA = glycolide
A: hydrophobic polymer (polylactide or copolymer of lactide and glycolide)
B: hydrophilic polymer (polyethylene glycol)

(2) A Block copolymer (PLDO-PEG-PLDO) made of a copolymer (PLDO) of lactide and 1,4-dioxan-2-one, and polyethylene glycol (PEG)

Lactide (10.54 g), 1,4-dioxan-2-one (7.46 g), polyethylene glycol (MW 1000, 7.5 g) and tin octoate (0.18 g), as the catalyst, were added to a two-necked, round-bottomed flask, which was then exposed to reduced pressure and filled with nitrogen gas. While heating at 80° C. to 120° C. with stirring, the mixture was reacted for 48 hours and then dissolved with chloroform. In order to precipitate the polymer, the resulting solution was added to dry ether. The precipitated polymer was separated, dissolved in chloroform and then purified by precipitation with ether. The precipitated polymer was separated and then dried under vacuum to obtain the block copolymer as shown in the following Table 2. Other block copolymers shown in Table 2 can be also prepared according to the same procedure as described above.

TABLE 2

| Block copolymer | LA/DO ratio | PEG MW (Daltons) | PEG (%) | MW (Daltons) A-B-A | Yield (%) |
|---|---|---|---|---|---|
| PLDO-PEG-1 | 75/25 | 1000 | 26.9 | 1360-1000-1360 | 93 |
| PLDO-PEG-2 | 50/50 | 1000 | 31.8 | 1070-1000-1070 | 90 |
| PLDO-PEG-3 | 20/80 | 1000 | 37.6 | 830-1000-830 | 89 |
| PLDO-PEG-4 | 80/20 | 3400 | 29.9 | 3980-3400-3980 | 95 |
| PLDO-PEG-5 | 70/30 | 3400 | 35.8 | 3050-3400-3050 | 93 |
| PLDO-PEG-6 | 50/50 | 3400 | 51.8 | 1580-3400-1580 | 96 |
| PLDO-PEG-7 | 30/70 | 8000 | 40.8 | 5800-8000-5800 | 98 |

Note)
LA = lactide, DO = 1,4-dioxan-2-one
A: hydrophobic polymer (copolymer of lactide and 1,4-dioxan-2-one)
B: hydrophilic polymer (polyethylene glycol)

Preparation 2: Synthesis of Liquid Polyethylene Glycol Derivatives (1) Synthesis of Diacetyl Polyethylene Glycol Polyethylene glycol (MW 300, 30 g, 0.1 mol) and acetic anhydride (24 g, 0.23 mol) and anhydrous zinc chloride (0.5 g) were added to a round-bottomed flask. After being refluxed for 12 hours, the mixture was dissolved in dichloromethane. The reaction mixture was then added to dry ether to cause precipitation of the oily product, which was then separated and purified with dry ether and then dried under vacuum (Yield: 100%; IR spectrum: 2980 (C—H), 1725 (C=O), 1150 (C—O) cm$^{-1}$).

(2) Synthesis of Disuccinyl Polyethylene Glycol

Polyethylene glycol (MW 300, 30 g, 0.1 mol) and succinic anhydride (22 g, 0.22 mol) were dissolved in dry acetone and then refluxed for 12 hours. The reaction mixture was distilled under reduced pressure to remove acetone. Dry ether was added to precipitate the synthesized product which was then dissolved in ethyl acetate and extracted with distilled water to obtain the final product The resulting product was then lyophilized (Yield. 99%; IR spectrum: 3500 (COO—H), 1725 (C=O), 1670 (C=O) cm$^{-1}$)

(3) Synthesis of Bis-Ethylsuccinyl Polyethylene Glycol

Disuccinyl polyethylene glycol (25 g, about 50 mmol) as prepared in the above (2) was dissolved in benzene, and then thionyl chloride (14 g, 117 mmol) was added. The mixture was refluxed for 12 hours and then distilled under vacuum to remove benzene The resulting reaction product was cooled to 0° C. and then excess ethanol (10 ml) was added. When reaction heat was no longer being generated, a condenser was added to the reaction vessel and the reaction mixture was refluxed for 30 minutes. Excess ethanol was removed and the resulting product was purified with dry ether obtaining the PEG derivative (PEG-SE) as shown in the following Table 3 (Yield: 98%; IR spectrum : 2990 (C—H), 1720 (C=O), 1200 (C—O), 1120 (C—O) cm$^{-1}$). Other liquid polyethylene glycol derivatives having the compositions as shown in the following Table 3 were synthesized according to the same procedures as described in (2) and (3) above.

TABLE 3

| PEG derivatives | PEG MW | Hydroxy protecting group | Ester group |
|---|---|---|---|
| PEG-SM | 300 | Succinic acid | Methyl |
| PEG-SE | 300 | Succinic acid | Ethyl |
| PEG-OE | 300 | Oxalic acid | Ethyl |
| PEG-AE | 600 | Adipic acid | Ethyl |
| PEG-GE | 600 | Glutaric acid | Ethyl |

Preparation of Injectable Liquid Polymeric Composition Containing Drugs

Example 1

100 mg of human growth hormone, 400 mg of the biodegradable block copolymer (PLA-PEG-1) synthesized above, 450 mg of liquid polyethylene glycol (MW 300) and 50 mg of gelatin were dissolved in 60% aqueous acetic acid solution obtaining a polymer solution. The polymer solution was then sterilized by filtering through a membrane filter having a pore size of 0.22 $\mu$m. The organic solvent and water were then removed from the polymer solution by lyophilization leaving a drug-containing liquid polymeric composition. The drug-containing liquid polymeric composition obtained was then filled in a sterilized disposable syringe in the amount of a single dose, which was then sealed.

Example 2

70 mg of human growth hormone, 300 mg of the biodegradable block copolymer (PLDO-PEG-2) synthesized above, 580 mg of dimethoxy polyethylene glycol (MW 300), 20 mg of zinc acetate and 30 mg of polysorbate-20 were dissolved in a 70% aqueous acetic acid solution and the drug-containing liquid polymeric composition was then prepared according to the same procedure as in Example 1.

Example 3

100 mg of porcine growth hormone, 320 mg of the biodegradable block copolymer (PLGA-PEG-2) synthesized above, 550 mg of diacetyl polyethylene glycol (DA-PEG, MW 300), 20 mg of zinc acetate and 10 mg of polysorbate-20 were dissolved in 40% aqueous acetic acid solution and the drug-containing liquid polymeric composition was then prepared according to the same procedure as Example 1.

Example 4

50 mg of ofloxacin, 200 mg of the biodegradable block copolymer (PLA-PEG-1) synthesized above, 700 mg of synthesized polyethylene glycol derivative (PEG-SM, MW 300) and 50 mg of sucrose were dissolved in a 70% aqueous ethanol solution and the drug-containing liquid polymeric composition was then prepared according to the same procedure as Example 1.

Example 5

200 mg of minocycline hydrochloride, 400 mg of the biodegradable block copolymer (PLGA-PEG-5) synthesized above and 400 mg of synthesized polyethylene glycol derivative (PEG-SE, MW 600) were dissolved in a 40% aqueous acetonitrile solution and the drug-containing liquid polymeric composition was then prepared according to the same procedure as Example 1.

Example 6

50 mg of cisplatin, 300 mg of the biodegradable block copolymer (PLGA-PEG-7) synthesized above, 550 mg of synthesized polyethylene glycol derivative (PEG-GE, MW 300), 50 mg of polysorbate-80 and 50 mg of dextran were dissolved in a 60% aqueous acetone solution and the drug-containing liquid polymeric composition was then prepared according to the same procedure as Example 1.

Example 7

60 mg of paclitaxel, 300 mg of the biodegradable block copolymer (PLA-PEG-1) synthesized above, 600 mg of polyethylene glycol (MW 300), 20 mg of poloxamer-188 and 20 mg of xylitol were dissolved in a 70% aqueous ethanol solution and the drug-containing liquid polymeric composition was then prepared according to the same procedure as Example 1.

Example 8

150 mg of piroxicam, 400 mg of the biodegradable block copolymer (PLDO-PEG-2) synthesized above, 420 mg of diacetyl polyethylene glycol (DA-PEG, MW 600) and 30 mg of gelatin were dissolved in a 50% aqueous acetic acid solution and the drug-containing liquid polymeric composition was then prepared according to the same procedure as Example 1.

Example 9

150 mg of diclofenac sodium, 300 mg of the biodegradable block copolymer (PLGA-PEG-5) synthesized above, 500 mg of polyethylene glycol (MW 600), and 50 mg of aluminum hydroxide were dissolved in a 50% aqueous ethanol solution and the polymeric composition was then prepared according to the same procedure as Example 1.

The drug-containing liquid polymeric compositions prepared above are shown in the following Table 4.

TABLE 4

| Composition | Physiologically active substance | Biodegradable block copolymer | Liquid polyethylene glycol derivative | Additive |
| --- | --- | --- | --- | --- |
| Example 1 | Human growth hormone (hGH) 10% | PLA-PEG-1 40% | PEG (MW 300) 45% | Gelatin (5%) |
| Example 2 | Human growth hormone (hGH) 7% | PLDO-PEG-2 30% | Dimethoxy PEG (MW 300) 58% | Zinc acetate (2%) Polysorbate 20 (3%) |
| Example 3 | Porcine growth hormone (pGH) 10% | PLGA-PEG-2 32% | DA-PEG (MW 300) 55% | Zinc chloride (2%) Polysorbate 20 (1%) |
| Example 4 | Ofloxacin 5% | PLA-PEG-1 20% | PEG-SM (MW 300) 70% | Sucrose 5% |
| Example 5 | Minocycline hydrochloride 20% | PLGA-PEG-5 40% | PEG-SE (MW 600) 40% | — |
| Example 6 | Cisplatin 5% | PLGA-PEG-7 30% | PEG-GE (MW 300) 55% | Polysorbate 80 (5%) Dextran (5%) |
| Example 7 | Paclitaxel 6% | PLA-PEG-1 30% | PEG (MW 300) 60% | Poloxamer 188 (2%) Xylitol (2%) |
| Example 8 | Piroxicam 15% | PLDO-PEG-2 40% | DA-PEG (MW 600) 42% | Gelatin (3%) |
| Example 9 | Diclofenac sodium 15% | PLGA-PEG-5 30% | PEG (MW 600) 50% | Aluminum hydroxide (5%) |

Test 1: In vitro Drug Release Test

Figure 1:
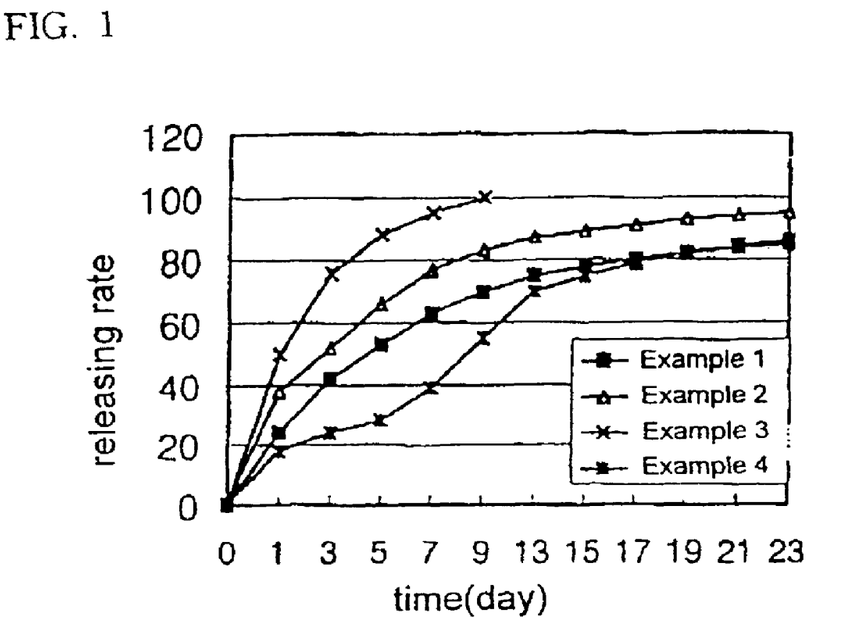
FIG. 1 shows the result of in vitro drug release tests for the liquid polymeric compositions of the present invention.

To prepare the respective drug-containing polymer mass, 0.5 ml of each of the drug-containing liquid polymeric compositions as prepared in Examples 1 to 4 was injected into 10 ml of phosphate buffer solution, pH 7.4, which was then allowed to stand in a water bath at 37° C. and shaken at the rate of about 50 rpm. The concentration of drug released after 1, 3, 12 and 24 hours, respectively, was measured. After 24 hours, the releasing medium was completely replaced and then the amount of released drug was measured at intervals of 24 hours. FIG. 1 shows the result of in vitro drug release test for the liquid polymeric compositions of the present invention. The results show that the drug contained in the polymer mass of the present invention is released at a relatively constant rate over a long period of time. For example, it takes between 9 (Example 1) to 23(Examples 2–4) days for the drug to be completely released from the polymer mass. Therefore, the liquid drug containing polymeric composition of the present invention is capable of forming a polymeric mass when contacted with an aqueous environment and is useful for sustained drug delivery.

Test 2: Test for Stability of the Liquid Polymeric Composition

The following test was conducted in order to identify whether the liquid polymeric composition of the present invention can be maintained in a stable state for a long period without causing phase separation.

(1) Preparation of Liquid Polymeric Composition

The liquid polymeric compositions prepared in the following Table 5, as Examples 10–13, were heated at 80° C. for one hour to prepare the uniform solutions.

(2) Preparation of Comparative Liquid Polymeric Composition

To prepare the uniform solutions, the liquid polymeric compositions as shown in the following Table 5, as Comparative Examples 1–3, were heated at 80° C. for five days according to the method of U.S. Pat. No. 5,607,686.

TABLE 5

| | Compositions | |
|---|---|---|
| Example 10 | PLA-PEG-PLA (1090-10000-1090) | 1 g |
| | Dimethyl polyethylene glycol (MW 350) | 5 g |
| Example 11 | PLGA-PEG-PLA (2500-3400-2500) | 1 g |
| | Bisethyl succinyl polyethylene glycol (MW 600) | 5 g |
| Example 12 | PLDO-PEG-PLDO (1360-1000-1360, LA/DO = 75/25) | 1 g |
| | Polyethylene glycol (MW 600) | 5 g |
| Comparative Example 1 | PLA (MW 6,400) | 1 g |
| | Dimethyl polyethylene glycol (MW 350) | 5 g |
| Comparative Example 2 | PLGA (LA/GA = 70/30, MW 3,600) | 1 g |
| | Diacetyl polyethylene glycol (MW 400) | 5 g |
| Comparative Example 3 | PLA (MW 2,500) | 1 g |
| | Dimethyl polyethylene glycol (MW 350) | 5 g |

(3) Determination of Stability

Each of the liquid polymeric compositions as prepared above were added to a cylindrical glass container having a diameter of 1 cm and a height of 5 cm to a height of 4 cm and then allowed to stand at 25° C. and then 4° C. At given times, 0.2 ml of each of both the supernatant and bottom solution were collected and then dissolved in 2 ml of distilled water and the content of the deposited hydrophobic polymer was analyzed. The stability of the composition was determined from the rate of contents of polymer in the bottom solution and the supernatant Specifically, when the rate of the content of polymer in the bottom solution/the content of polymer in the supernatant was 1.0, the composition was determined to be stable, whereas at a rate below 1.0, it was determined that the phase separation had occurred. The result thereof is shown in FIG. 2.

Figure 2:
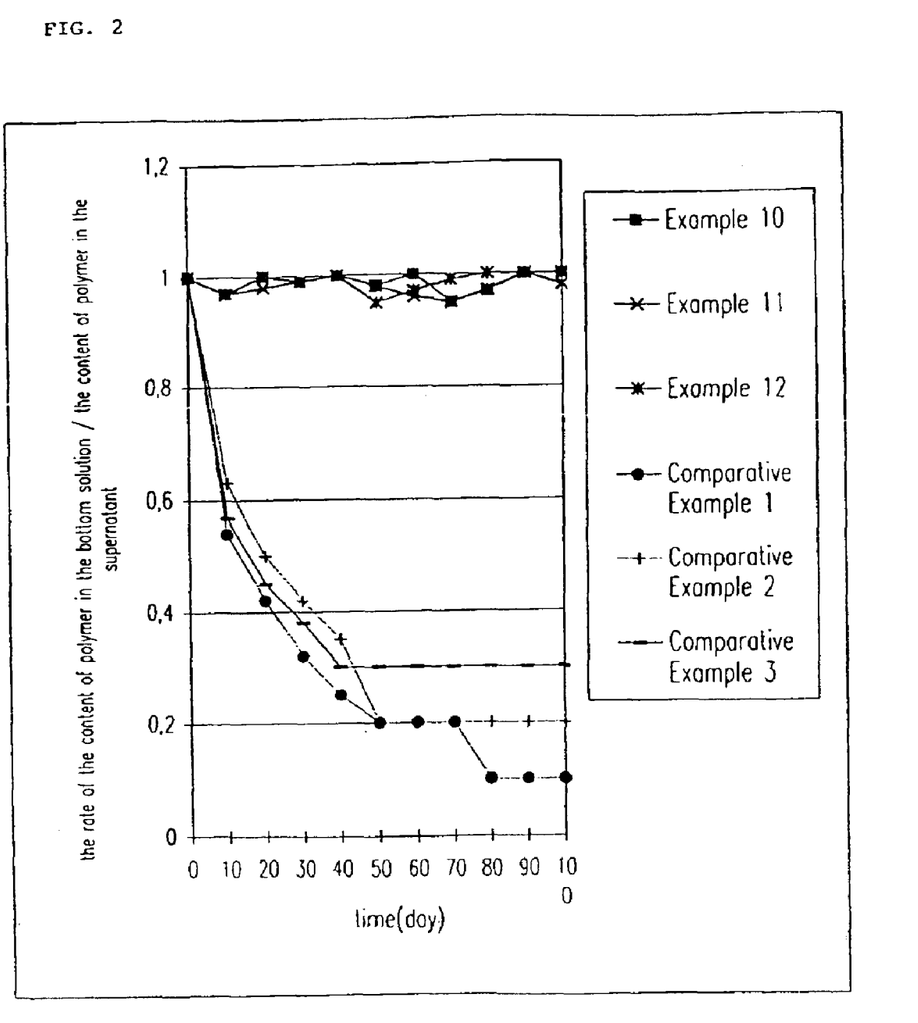
FIG. 2 shows the result of stability tests for the liquid polymeric composition of the present invention.

From FIG. 2, it can be seen that the compositions of the present invention maintain a uniform composition over 100 days whereas in all of the comparative compositions phase separation occurs between 10 and 30 days.

Since, in the liquid polymeric composition according to the present invention, the biodegradable block copolymer is dissolved in a low molecular polyethylene glycol, the composition can be sterilized by membrane filtration and directly implanted through a simple injection. The drug can be slowly released from the implant which can then decompose into materials harmless to the human body and be excreted after the drug is completely released. Therefore, the liquid polymeric composition of the present invention is very useful as sustained delivery system for physiologically active substances such as peptides and proteins.

While the invention has been described with respect to the above specific embodiments, it should be recognized that various modifications and changes may be made to the invention by those skilled in the art which also fall within the scope of the invention as defined by the appended claims.

What is claimed is:

1. A liquid polymeric composition capable of forming a physiologically active substance-containing implant in a living body, said composition comprising a water-soluble biocompatible liquid polyethylene glycol derivative, a biodegradable block copolymer comprising a di- or tri-block copolymer, which comprises a biodegradable hydrophobic polymer A block component and a hydrophilic polymer B block component, wherein the hydrophilic polymer B block is a member selected from the group consisting of polyethylene glycol (PEG), a copolymer of ethylene glycol and propylene glycol and derivatives thereof, wherein said biodegradable block copolymer is insoluble in water but soluble in said water-soluble biocompatible liquid polyethylene glycol derivative and a physiologically active substance.

2. The composition of claim 1, wherein the liquid polyethylene glycol derivative is in an amount sufficient to solubilize said biodegradable block copolymer and said physiologically active substance.

3. The composition of claim 2, wherein the liquid polyethylene glycol derivative is within the range of 10 to 95 wt %; the biodegradable block copolymer is within the range of 5 to 80%; the physiologically active substance is within the range of 1 to 40 wt % based on the total weight of said composition.

4. The composition of claim 3, wherein the liquid polyethylene glycol derivative is within the range of 30 to 70 wt %; the biodegradable block copolymer is within the range of 20 to 50%; the physiologically active substance is within the range of 1 to 40 wt % based on the total weight of said composition.

5. The composition of claim 1, wherein the hydrophobic polymer A block is a member selected from the group consisting of L-polylactide (L-PLA), D,L-polylactide (D,L-PLA), a copolymer of L- or D,L-lactide with glycolide (PLLGA or PDLLGA), polyglycolide (PGA), polycaprolactone (CL), a copolymer of lactic acid with caprolactone (PLCL), polyhydroxy butyric acid (PHB), a copolymer of 1,4-dioxan-2-one with lactide (PLDO), and poly(p-dioxanone) (PDO).

6. The composition of claim 1, wherein the hydrophobic polymer A block has an average molecular weight within the range of 500 to 25,000 Daltons.

7. The composition of claim 1, wherein the hydrophilic polymer B block has an average molecular weight within the range of 100 to 10,000 Daltons.

8. The composition of claim 1, wherein the hydrophilic polymer B block is within the range of 20 to 80% wt % based on total weight of the biodegradable block copolymer.

9. The composition of claim 1, wherein the liquid polyethylene glycol derivative has the following formula (I):

(I)

wherein $R^1$ is $H_2$ $(CH_2)_mCH_3$ or $CO(CH_2)_mCH_3$, wherein m is an integer of 0 to 17; X is O, NH or S; and 1 is an integer of 1 to 100.

10. The composition of claim 1, wherein the liquid polyethylene glycol derivative has the following formula (II):

(II)

wherein $R^2$ is $(CH2)_xCH_3$, wherein x is an integer of 0 to 17, H, Na, Ca, Mg or Zn; p is an integer of 1 to 100; and q is an integer of 0 to 6.

11. The composition of claim 1, wherein the liquid polyethylene glycol derivative has an average molecular weight within the range of 200 to 1,000 Daltons.

12. The composition of claim 1, wherein the physiologically active substance is a member selected from the group consisting of peptide or protein drugs, antibacterial agents, anticancer agents and anti-inflammatory agents.

13. The composition of claim 12, wherein the peptide or protein drug is a member selected from the group consisting of human growth hormone (hGH), porcine growth hormone (pGH), leukocyte growth factor (G-CSF), erythrocyte growth factor (EPO), macrophage growth factor (M-CSF), tumor necrosis factor (TNF), epithelial growth factor (EGF), platelet-derived growth factor (PDGF), interferon-α, β, γ(IFN- α, β, γ), interleukin-2 (IL-2), calcitonin, nerve growth factor (NGF), growth hormone releasing factor (QBf) angiotensin, luteinizing hormone releasing hormone (LHRH), LHRH antagonist, insulin, thyrotropin releasing hormone (TRH), angiostatin, endostatin, somatostatin, glucagon, endorphin, bacitracin, mergain, colistin, bone growth factor (BMP) and mixtures thereof.

14. The composition of claim 12, wherein the antibacterial agent is a member selected from the group consisting of minocycline, tetracycline, ofloxacin, phosphomycin, mergain, profloxacin, ampicillin, penicillin, doxycycline, thienamycin, cephalosporin, norcadicin, gentamycin, neomycin, kanamycin, paromomycin, micronomycin, amikacin, tobramycin, dibekacin, cefotaxim, cephaclor, erythromycin, ciprofloxacin, levofloxacin, enoxacin, vancomycin, imiphenem, fucidic acid and mixtures thereof.

15. The composition of claim 12, wherein the anticancer agent is a member selected from the group consisting of paclitaxel, taxotare, adriamycin, endosatin, angiostatin, mitomycin, bleomycin, cisplatin, carboplatin, doxorubicin, daunorubicin, idarubicin, 5-fluorouracil, methotrexate, actinomycin-D and mixtures thereof.

16. The composition of claim 12, wherein the anti-inflammatory agent is a member selected from the group consisting of lysozyme, acetaminophen, aspirin, ibuprofen, disciofenac, indomethacin, prioxicain, fenoprofen, flubiprofen, ketoprofen, naproxen, suprofen, loxoprofen, cinoxicam, tenoxicam and mixtures thereof.

17. The composition of claim 1, further comprising a pharmaceutically acceptable additive selected from the group consisting of surfactants, inorganic salts, sugars, natural polymers and mixtures thereof.

18. The composition of claim 17, wherein the surfactant is a member selected from the group consisting of polysorbate, sodium dodecylsulfate, polyvinyl pyrrolidone, poloxarners, glyceryl monooleate, glyceryl monostearate, polyoxyethylene alkyl ether and mixtures thereof.

19. The composition of claim 17, wherein the inorganic salt is a member selected from the group consisting of sodium chloride, calcium chloride, zinc chloride, magnesium chloride, calcium carbonate, zinc carbonate, zinc acetate, zinc lactate, magnesium hydroxide, aluminum chloride, aluminum hydroxide, zinc oxide and mixtures thereof.

20. The composition of claim 17, wherein the sugar is a member selected from the group consisting of mannitol, sorbitol, glucose, xylitol, trehalose, sorbose, sucrose, galactose, dextran, dextrose, fructose, lactose and mixtures thereof.

21. The composition of claim 17, wherein the natural polymer is selected from the group consisting of cyclodextrin, gelatin, albumin, hyaluronic acid, chitosan, sodium carboxymethylcellulose and mixtures thereof.

22. The composition of claim 17, wherein the additive is within the range of 0.01 to 10 wt % based on the total weight of said composition.

23. A formulation for an implant comprising the composition of claim 1.

24. An implant formed from the composition of claim 1.

25. A process for preparing a liquid polymer composition for implant comprising the steps of mixing and dissolving a water-soluble biocompatible liquid polyethylene glycol derivative, a biodegradable block copolymer which is insoluble in water but soluble in said water-soluble biocompatible liquid polyethylene glycol derivative, and a pharmacologically or physiologically active substance, in an organic solvent or mixture of an organic solvent and water to obtain a polymeric solution wherein the ratio of the organic solvent and water is within the range of 0.2/0.8 to 0.8/0.2; sterilizing the polymeric solution by filtration through a membrane and removing the organic solvent by lyophilizing or evaporating the filtered polymeric solution wider reduced pressure.

26. A process of preparing a liquid polymeric composition for implant comprising the steps of preparing a solution of one or more member selected from the group consisting of a water-soluble biocompatible liquid polyethylene glycol derivative, a biodegradable block copolymer which is insoluble in water but soluble in said water-soluble biocompatible liquid polyethylene glycol derivative, and a physiologically active substance, in an organic solvent or mixture of an organic solvent and water to obtain a solution wherein the ratio of the organic solvent and water is within the range of 0.2/0.8 to 0.8/0.2; sterilizing the respective solution by filtration through a membrane; mixing the filtered solution and removing the organic solvent by lyophilizing or evaporating the mixed solution under reduced pressure.

27. The process of claim 25, wherein the organic solvent is a member selected from the group consisting of acetonitrile, acetone, acetic acid, dimethyl acetamide, ethanol, isopropanol, dioxane and mixtures thereof.

28. The process of claim 25, wherein the membrane filter has a pore size within the range of 0.8 to 0.22 μm.

29. The process of claim 26, wherein the organic solvent is a member selected from the group consisting of acetonitrile, acetone, acetic acid, dimethyl acetamide, ethanol, isopropanol, dicxane and mixtures thereof.

30. The process of claim 26, wherein the membrane filter has a pore size within the range of 0.8 to 0.22 μm.

31. A liquid polymeric composition which is stable at room temperature and which is capable of forming a physiologically active substance-containing implant in a living body, said composition comprising a water-soluble biocompatible liquid polyethylene glycol derivative, a biodegradable block copolymer which is insoluble in water but soluble in said water-soluble biocompatible liquid polyethylene glycol derivative and a physiologically active substance, wherein the biodegradable block copolymer is formed by an ester bonding of a hydrophobic polyester A block and a hydrophilic polyethylene glycol B block.

32. The composition of claim 12 wherein the peptide or protein drug is a vaccine.

33. The composition of claim 12 wherein the peptide or protein drug is a monoclonal antibody.

* * * * *